United States Patent [19]
Morcos

[11] Patent Number: 5,807,536
[45] Date of Patent: Sep. 15, 1998

[54] ANATOMICAL IMAGING WITH PHYCOCYANINS

[75] Inventor: Nabil Charle Morcos, Irvine, Calif.

[73] Assignee: The Regents of the University of California, Oakland, Calif.

[21] Appl. No.: 631,670

[22] Filed: Apr. 9, 1996

[51] Int. Cl.$^6$ .......................... A61K 51/00; A61M 36/14
[52] U.S. Cl. .......................... 424/1.65; 424/9.1; 424/9.4; 424/9.5; 424/9.6; 424/9.3
[58] Field of Search ................... 424/1.11, 1.65, 424/9.1, 9.3, 9.4, 9.5, 9.6; 435/257.1

[56] References Cited

U.S. PATENT DOCUMENTS

| | | | |
|---|---|---|---|
| 4,336,809 | 6/1982 | Clark | 128/665 |
| 4,512,762 | 4/1985 | Spears | 604/21 |
| 4,745,285 | 5/1988 | Recktenwald et al. | 250/458.1 |
| 4,886,831 | 12/1989 | Morcos et al. | 514/456 |
| 5,163,898 | 11/1992 | Morcos et al. | 604/20 |
| 5,489,525 | 2/1996 | Pastan | 435/7.23 |

OTHER PUBLICATIONS

Fuchs et al (1988), Am. Rev. Respir. Dis., vol. 138, No. 5, pp. 1124–1128, "Use of Allophycocyanin Allows Quantitative Description by Flow Cytometry of Alveolar Macrophage Surface Antigens Present in Low Numbers of Cells".

*Primary Examiner*—John Kight
*Assistant Examiner*—Dameron Jones
*Attorney, Agent, or Firm*—Daniel L. Dawes

[57] ABSTRACT

Phycocyanins selectively impregnate biological structures including atherosclerotic plaque and tumors. Imaging of biological structures can be enhanced by tagging to a phycocyanin an atom which is compatible with the or complementary to any of the imaging modalities. The tagged phycocyanin can then be administered to a subject. The improvement can be utilized to enhance images of all structures, arterial wall thickness, atherosclerotic plaque, luminal boundaries and to better delineate tumors mass outlines.

27 Claims, 1 Drawing Sheet

ANATOMICAL IMAGING WITH PHYCOCYANINS

BACKGROUND OF THE INVENTION

1. Field of the Invention

The present invention relates to the field of radiographic imaging of biological structures, and particularly to a method of imaging arterial lumens, atherosclerotic plaque and tumors.

2. Description of the Prior Art

The radiographic visualization of biological structures assists the diagnosis and treatment of a variety of medical diseases. Thus, there is considerable effort in the medical community to obtain safe, noninvasive and effective methods for radiographically imaging biological structures in the diagnosis and treatment of medical diseases. Enhancement of the quality of images obtained by presently available technologies is constantly at the forefront. Two such diseases in particular where these types of methods for radiographic imaging would be most advantageously applied are atherosclerosis and cancer.

Atherosclerosis is a disease associated with narrowing or occlusion of blood vessels, arteries and the like in which fatty substances, particularly lipids, form deposits in the vessels. Such deposits are commonly referred to as arteriosclerotic plaques. Generally, these plaques form as a result of lipids being deposited in and beneath the membrane lining of these vessels. Generally, atherosclerosis involves medium and large-size vessels with the most commonly affected being the aorta, iliac, femoral, coronary, and cerebral arteries. If the disease is not checked, tissues or organs that are distal to the atherosclerotic plaque experience reduced blood flow, and thus are adversely affected.

Angiography is a medical procedure used to visualize blood vessels in the diagnosis of such conditions as cerebrovascular attack (stroke) and myocardial infarction. One form of the procedure is to insert a catheter into a blood vessel and introduce a contrast material, such as an iodine-based dye, into the circulatory system. The dye roughly outlines the vessel lumens which are photographed by x-rays. This method, however, is risky and invasive. In addition, it is not always possible to accurately view a particular region of the artery or the wall thickness, since it is not possible to control the location of the concentration of the dye.

Another method for visualizing arterial wall thickness, and hence plaque location and thickness, involves inserting an intravascular ultrasound probe into the artery to visualize a particular segment. This procedure, however, is extremely invasive and insertion of the probe into a partially blocked artery is not always possible.

What is needed is a method for radiographic imaging of arterial obstructions that is effective and noninvasive in the diagnosis and treatment of atherosclerosis and cancer. It is an overall object of the present invention to enhance images of most biological structures obtained by all imaging modalities now known or later devised and in particular to provide a method for visualizing arterial lumens, arterial wall thickness and the location and thickness of arteriosclerotic plaque. A further object of the invention is to provide a method for noninvasively visualizing tumor masses, their location and size. Another object of the invention is to provide a method for permitting instantaneous monitoring of the progress of interventions on either plaque or tumors.

BRIEF SUMMARY OF THE INVENTION

The invention exploits the fact that phycocyanins have been found to impregnate biological structures and in particular to be impregnated in the structure's volume rather than being limited to a surface. By tagging or attaching an appropriate marker to the phycocyanin as determined by the chosen imaging modality it becomes possible for the first time to clearly image all the boundaries of a biological structure as well as the overall topology of the biological structure. The invention has particular utility in that imaging of both the inside and outside walls of vascular structures and tumor bearing biological structures are reliably, clearly and safely delineated.

The invention provides a method for effective and noninvasive radiographic imaging of biological structures, including arteriosclerotic plaque and tumors. The method utilizes phycocyanin, a compound known to selectively adhere to atherosclerotic plaque and tumors. The method comprises the steps of labeling phycocyanin with a specific atom known to enhance the images from the imaging modality chosen. For example, in the case of atherosclerotic plaque, a radio-opaque atom, iodine, and administering an amount of the labeled phycocyanin to a patient, which amount is effective to contact the biological structure. The phycocyanin selectively impregnates the atherosclerotic plaque and cancer cells in the biological structure. The biological structure is then subjected to radiography and effectively and noninvasively viewed.

The invention is a method for radiographically imaging a biological structure comprising the steps of labeling phycocyanin with a radio-opaque atom, and administering an effective amount of the labeled phycocyanin to a patient to effect contact and impregnation of the labeled phycocyanin with the biological structure. The biological structure is radiographed or a visual pattern of the labeled phycocyanin otherwise created. As a result, the biological structure can be fully and accurately imaged.

The step of administering the labeled phycocyanin comprises administering it in a physiologically compatible solution.

The step of administering the labeled phycocyanin to the biological structure comprises contacting an arterial lumen with the phycocyanin, or a tumor mass.

In the preferred embodiment the step of labeling the phycocyanin labels the phycocyanin with iodine.

The step of administering comprises the step of intravascularly, intraperitoneally or intravenously injecting the labeled phycocyanin.

Preferably in the step of administering the labeled phycocyanin, the dosage of the labeled phycocyanin administered does not exceed 0.5 gm/kg of body weight of the patient.

In the step of radiographing the biological structure a radiographic image of the luminal boundaries of the arterial lumen, the wall thickness of the arterial lumen, or atherosclerotic plaque in the arterial lumen is created.

In one embodiment the method further comprises the step of radiating the phycocyanin in contact with the tumor mass to effect destruction of tumor cells.

The invention can also be characterized as an improvement in a method for radiographically imaging a biological structure into which an effective amount of a radiographically opaque substance has been impregnated comprising the steps of preferentially impregnating said biological structure with radiographically labeled phycocyanin; and imaging said biological structure so that portions of said biological structure impregnated thereby produce an enhanced delineation from surrounding portions of said biological structure not impregnated by said radiographically labeled phycocyanin.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. The invention may be better visualized by now turning to the following drawings wherein like elements are referenced by like numerals.

Figure 1:
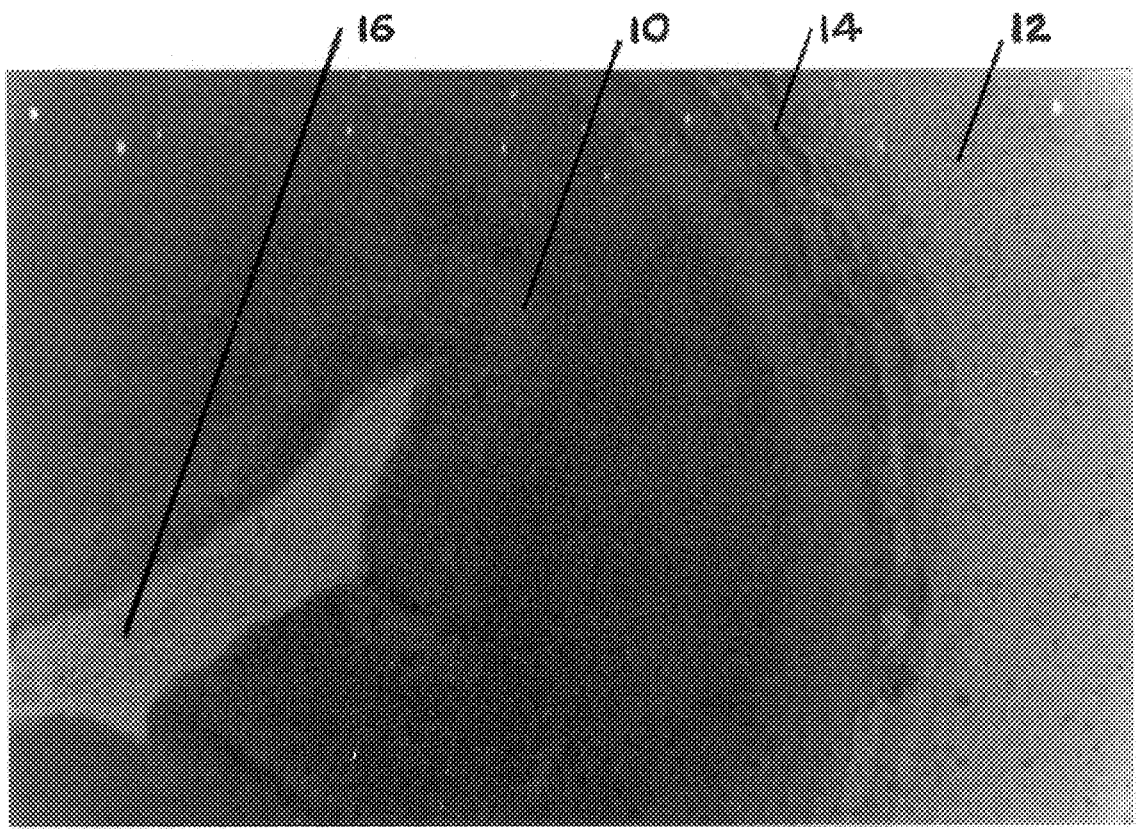
FIG. 1 is a light microscopic image of a cross section through an atherosclerotic human artery which has been exposed to a physiological salt solution without phycocyanin.

The invention and its various embodiments can now be understood by turning to the following detailed description.

DETAILED DESCRIPTION OF THE PREFERRED EMBODIMENTS

Phycocyanins selectively impregnate biological structures including atherosclerotic plaque and tumors. Radiographic imaging of these biological structures is possible by chemical labeling of phycocyanins administered to a patient with an atom or atoms appropriate to the imaging modality desired or used. The phycocyanins are labeled with a radio-opaque atom, such as iodine, a radioactive atom such as technetium 99 m, a paramagnetic complex of manganese, or an acoustically echo dense atom such as calcium. The method can be used to image all biological structures in general including arterial wall thickness, luminal boundaries, plaque and tumors.

The enhancement of biological images provided by the invention may be implemented in the context of many different imaging modalities including but not limited to fluoroscopy, computerized tomography scanning (CT-scanning), ultrafast computerized tomography scanning (ultrafast CT-scanning), magnetic resonance imaging (MRI), nuclear radiology imaging including single photon emission tomography (SPECT imaging), and ultrasonic imaging. Vascular and tumor mass imaging is also two of many specific applications where the imaging enhancement has particular utility.

For example in fluoroscopy, computerized tomography scanning (CT-scanning), and ultrafast computerized tomography scanning (ultrafast CT-scanning) phycocyanins are linked to a heavy atom such as iodine 123 at a ratio between 1.5 and 6 iodine atoms per phycocyanin molecules. The linkage procedure, iodination, employs standardly available procedures used by the radiocontrast industry. See for example, Binz A. et.al..: Ueber Biochemische Eigneschaften von Derivaten des Pyridins und Chinolins, Biochem. Z. 203:218 (1928); and Machulla H. et.al., Biochemica Concept and Synthesis of a Radioiodinated Phenyl Fatty acid for in Vivo Metabolic Studies of the Myocardium, Eur. J. Nucl. Med. 5:171 (1980). The tagged phycocyanins are administered in saline solution intravenously, intraarterially or intraperitoneally.

In magnetic resonance imaging (MRI), paramagnetic agents, such as manganese, iron or gadolinium are attached to centers of metal chelates which in turn are attached to the phycocyanins using conventional procedures. Such paramagnetic centers have been successfully linked to albumin and concanvalin A, which are large proteins similar to phycocyanin. See, Schmeidl U. et.al., "*Comparison of Initial Biodistribution Patterns of Gd-DPTA and Albumin (Gd-DPTA) Using Rapid Spin Echo MR Imaging,*" J.Comput. Assist. Tomogr. 11, 306 (1987); and Koenig S. H., et.al., "*Investigation of the Biochemical State of Paramagnetic Ions in vivo Using Magnetic Field Dependence of 1/T1 of Tissue Protons (NRMD Profile): Applications to Contrast Agents for Magnetic Resonance Imaging,*" Nucl. Med. Bio. Int. Radiat. Appl. Instrm. (part B) 15:23 (1988). Paramagnetic centers have also been linked to dextran, a long chain carbohydrate. See, Gibby et.al., "*Cross-linked DTPA Polysacchariends for Magnetic Resonance Imaging, Synthesis and Relaxation Properties,*" Invest. Radiol. 24:302 (1989), and linked to other organic molecules such as organic nitroxide compounds. See, Brasch R. C. et.al., "*Nuclear Magnetic Resonance Study of a Paramagnetic Nitroxide Contrast Agent for Enhancement of Renal Structures in Experimental Animals,*" Radiol. 147:773 (1983).

In nuclear radiology imaging and positron emission tomography, phycocyanins are liked to radioisotope tracers to enhance radiographic images obtained by either a gamma camera or by single photon emission computerized tomography (SPECT imaging). Known radionuclide tracers include technetium 99 m, indium 111, thallium 201, iodine 125, 123 and 131, and phosphorous 32. Phycocyanins may also be linked to positron emitting isotopes such a fluorine 18, rubidium 82, and nitrogen 13 for positron emission tomography studies (PET). Technetium 99 m may be linked to proteins such a phycocyanins using the procedure of Khaw, et.al., "*Scintigraphic Quantification of Myocardial Necrosis in Patients after Intravenous Injection of Mysoin Specific Antibody,*" Circulation 74:501 (1986). Indium 111 labeling of phycocyanin may be performed using the procedure of Knight for labeling proteins. See, Knight et.al., "*Imaging Thrombi with Radiolabelled Antifibrin Monoclonal Antibodies*" Nucl. Med Commun. 9:823 (1988). Many commercial procedures are available to link the iodine radioisotopes to organic molecules, such as shown by Machulla H., et.al., "*Biochemical Concept and Synthesis of a Radioiodinated Phenyl Fatty Acid for in Vivo Metabolic Studies of the Myocardium*", Eur. J. Nucl. Med. 5:171 (1980) and to proteins such as phycocyanins. See, Marchalonis et.al. "*An Enzymatic Method for the Trace Iodination of Immunoglobulins and other Proteins*", Biochem. J. 113:299 (1969) and Hunter et.al., "*Preparation of Iodine* 131 *Labeled Human Growth Hormone of High Specific Activity*", Nature (London) 194:495 (1962).

In the case of ultrasonic imaging phycocyanin saline solutions are intravenously injected which have either been sonicated to create microbubbles or labeled with an echo dense atom such as calcium. The portions of the images that are enhanced will be dependent on the unique distribution mode of phycocyanins. A sonicated albumin based solution, Albunex, is commercially available as an ultrasonic contrast agent from Molecular Biosystems Inc. of Sand Diego, Calif. Since phycocyanins are proteins similar to albumin, a sonicated ultrasonic contrast solution may be prepared from phycocyanin using similar technology. See, Feinstein et.al., "*Albunex: A New Intravascular Ultrasound Contrast agent; Preliminary Safety and Efficacy Results*" Circulation 4 (Suppl II) 565 (1988); and Feinstein, et.al., "*Sonicated Echocardiographic Solution Agents. Reproducibility Studies,*" J. AmSoc. Echo. 2:215 (1989).

Since phycocyanins specifically impregnate biological structures, particularly atherosclerotic plaque and tumor structures, subsequent irradiation or activation of these compounds can be used to selectively destroy cancer cells. This cytotoxic effect can cause plaque disintegration and reduction in tumor mass. The medical uses of phycocyanin based upon their cytotoxic effect are described in U.S. Pat. Nos. 4,886,831 and 5,163,898, expressly incorporated herein by reference.

It will be appreciated that the term phycocyanin and phycocyanins referred to as blue and red phycocyanins and phycoerythrins, which are a protein-bound pigment having an open-chain tetrapyrrole structure and a blue or red coloration, which can be used in solution. Phycocyanins are a member of a broader class of similar compounds termed phycobilins. Because of the similar chemical structures of the members of this group, it is anticipated that a large number of chemicals in the group can be substituted for phycocyanin in the instant invention, and the definition of phycocyanin is intended to encompass related materials having similar selective retention properties in this present method. Phycocyanin can be obtained commercially from several sources, one of which is Sigma Chemical Company of St. Louis, Mo.

The phycocyanin is chemically labeled with a radio-opaque atom, preferably high density iodine. The chemically labeled phycocyanins are produced by iodination or equivalent reaction. Similar organic molecules labeled with radio-opaque substances are sold as Hexabrix (ioxaglic acid) and Optiray (leversol) manufactured by Mallinkrodt Inc. of St.Louis, Mo., and Omnipaque (iohexol) manufactured by Zycomed, New York, N.Y., which may be used as the matrix carrying iodine in the labeling procedures to provide iodine tagged phycocyanins.

The chemically labeled phycocyanin is administered to a patient so as to effect contact with the biological structure to be viewed. Depending on the type of biological structure that is sought to be imaged, phycocyanin can be injected intravenously, intravascularly or intraperitoneally in the region of the biological structure to be imaged. The compound may be used alone or in a physiologically compatible solution, such as saline.

The concentration of phycocyanin in the tissue to produce optimum effects will vary on the type, size and location of the biological structure to be viewed. Preferably, the amount or dose of phycocyanin should be less than about 0.5 gm/kg of body weight to provide optimum effects. The amount should be sufficient to contact the biological structure and permit the phycocyanin to impregnate the target cells. Enhanced radiographic viewing of the tagged biological structure will then be possible. Doses as low as 0.05 gm/kg of body weight are likely sufficient, with a practical dose of about 0.25 gm/kg of body weight. Doses in excess of 0.5 gm/kg of body weight should be avoided, as the safe dosage (50% lethal dose, $LD_{50}$) of phycocyanin may be exceeded.

It will be appreciated that virtually any type of biological structure can be radiographically imaged by the method of the invention. The invention is considered particularly useful in the radiographic imaging of arterial lumens and tumors. Visualization of the full arterial wall thickness and hence plaque location and thickness is made possible by the method of the invention, otherwise not possible by conventional angiography. Luminal boundaries are imaged noninvasively.

It is also envisioned that radiographic viewing using chemically labeled phycocyanin may be performed in conjunction with irradiation treatment. The progress of cancer and atherosclerosis treatment can be followed by radiographically viewing the tumor or arterial plaque either simultaneously or following the irradiation of the phycocyanin to treat these sites. Enhancement of imaging by any method now known or later devised using appropriately tagged phycocyanins is within the scope of the invention, e.g. any of the x-ray, cat scan, nuclear, ultrasound or nuclear magnetic resonance imaging techniques with the corresponding effective tags conjugated or linked to phycocyanin for the imaging modality employed can be used.

The invention is further embodied in the following non-limiting examples.

EXAMPLE 1

Uptake of Phycocyanin Into Human Atherosclerotic Plaque

Figure 2:
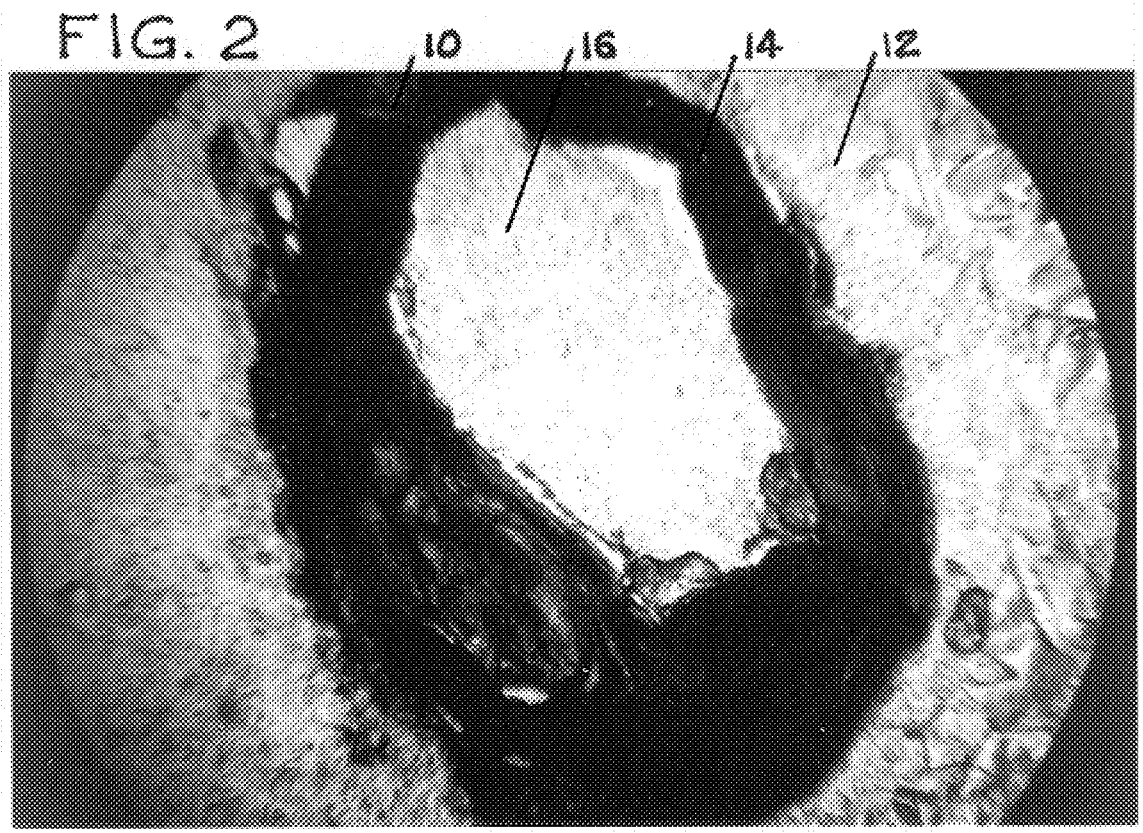
FIG. 2 is the selective uptake of phycocyanin in an atherosclerotic plaque.

The selective concentration of phycocyanin in atherosclerotic plaque was demonstrated by incubating a segment of a human atherosclerotic coronary artery obtained at autopsy with 0.1 mg/ml of phycocyanin in a suitable physiologically compatible buffer. Another segment of the human artery was exposed to a physiological salt solution without phycocyanin. FIG. 1 is a light microscopic image of a cross section through the segment that was not treated with phycocyanin. FIG. 2 is a light micrograph of a cross section of the segment that was treated with the phycocyanin solution. It is clearly seen that phycocyanin, represented by the darker areas 10, is predominantly located in the plaque regions, and only appears in lesser amounts at the artery walls 12 associated with the thin muscle coat 14.

EXAMPLE 2

Toxicity Using Iodine-labeled Phycocyanin

Studies were done to determine the half lethal dose, $LD_{50}$, or the concentration of phycocyanin, which kills 50% of the mice treated with phycocyanin, using standard techniques well known to those skilled in the art. Approximately 0.3 gm of phycocyanin per kilogram was determined to be the $LD_{50}$ for mice when the drug was administered intravenously. Similar studies were conducted on mice which received intraperitoneal injections of phycocyanin. The $LD_{50}$ for this route of administration was determined to be about 0.5 gm/kg.

In addition to the above study, the toxicity of phycocyanin to heart tissue was determined. The study consisted of isolating a beating rabbit heart, and perfusing the heart with a suitable saline solution of 64 micromolar phycocyanin for fifteen minutes. There was no effect on the viability of the heart as measured by its contractile properties.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method for imaging a biological structure comprising the steps of:
   labeling phycocyanin with a tagged atom detectable by a selected imaging modality;
   administering an effective amount of the labeled phycocyanin to a patient so that said labeled phycocyanin can impregnate the biological structure; and
   imaging the biological structure to create an image of the biological structure using said selected imaging modality, whereby said biological structure can be delineated.

2. The method for imaging a biological structure of claim 1, wherein said labeled phycocyanin is administered in a physiologically compatible solution.

3. The method for imaging a biological structure of claim 1, wherein said phycocyanin is administered into an arterial lumen.

4. The method for imaging a biological structure of claim 1, wherein said phycocyanin is administered to contact a tumor mass.

5. The method for imaging a biological structure of claim 1, wherein said phycocyanin is labeled with iodine.

6. The method for imaging a biological structure of claim 1, wherein said labeled phycocyanin is injected intravenously.

7. The method for imaging a biological structure of claim 1, wherein said labeled phycocyanin is injected intravascularly.

8. The method for imaging a biological structure of claim 1, wherein said labeled phycocyanin is injected intraperitoneally.

9. The method for imaging a biological structure of claim 1, wherein dosage of the labeled phycocyanin administered does not exceed 0.5 gm/kg of body weight of said patient.

10. The method for imaging a biological structure of claim 3, wherein a radiographic image of luminal boundaries of said arterial lumen is created.

11. The method for imaging a biological structure of claim 3, wherein a radiographic image of wall thickness of said arterial lumen is created.

12. The method for imaging a biological structure of claim 3, wherein a radiographic image of atherosclerotic plaque in said arterial lumen is created.

13. The method for imaging a biological structure of claim 4 further comprising the step of irradiating said phycocyanin in contact with the tumor mass to destroy tumor cells.

14. The method of claim 1, wherein said selected imaging modality comprises imaging by fluoroscopy.

15. The method of claim 1, wherein said selected imaging modality comprises imaging by computerized tomography scanning (CT-scanning).

16. The method of claim 1, wherein said selected imaging modality comprises imaging by ultrafast computerized tomography scanning (ultrafast CT-scanning).

17. The method of claim 1, wherein said selected imaging modality comprises imaging by magnetic resonance imaging (MRI).

18. The method of claim 1, wherein using said selected imaging modality comprises imaging by nuclear radiology imaging.

19. The method of claim 1, wherein using said selected imaging modality comprises imaging by single photon emission tomography (SPECT imaging).

20. The method of claim 1, wherein using said selected imaging modality comprises imaging by ultrasonic imaging.

21. An improvement in a method for radiographically imaging a biological structure into which an effective amount of a radiographically opaque substance has been impregnated comprising the steps of:
    impreanating said biological structure with phycocyanin labeled with a radiographically opaque substance; and
    radiographically imaging said biological structure so that portions of said biological structure are delineated.

22. The improvement of claim 21, wherein said labeled phycocyanin is administered in a physiologically compatible solution.

23. The improvement of claim 21, wherein said labeled phycocyanin is administered into an arterial lumen.

24. The improvement of claim 23, wherein said labeled phycocyanin is administered to a patient in a dosage not exceeding 0.5 gm/kg of body weight of said patient.

25. The improvement of claim 23, wherein a radiographic image of luminal boundaries of said arterial lumen is created.

26. The improvement of claim 23, wherein a radiographic image of wall thickness of said arterial lumen is created.

27. The improvement of claim 23, wherein a radiographic image of atherosclerotic plaque in said arterial lumen is created.

* * * * *